US008268305B1

(12) United States Patent
Schuler et al.

(10) Patent No.: US 8,268,305 B1
(45) Date of Patent: Sep. 18, 2012

(54) METHOD AND COMPOSITIONS TO REDUCE SERUM LEVELS OF TRIACYLGLYCERIDES IN HUMAN BEINGS USING A FUNGAL LIPASE

(75) Inventors: Christopher Schuler, Charlottesville, VA (US); Edward Schuler, Keswick, VA (US); Christopher S. Penet, Manakin Sabot, VA (US); Gregory Moore, Charlottesville, VA (US); Kelly Gregory, Mineral, VA (US)

(73) Assignee: Bio-Cat, Inc., Troy, VA (US)

( * ) Notice: Subject to any disclaimer, the term of this patent is extended or adjusted under 35 U.S.C. 154(b) by 0 days.

(21) Appl. No.: 13/244,131

(22) Filed: Sep. 23, 2011

(51) Int. Cl.
*A61K 38/46* (2006.01)
*A61K 38/48* (2006.01)
*A61K 38/54* (2006.01)
*A61K 47/00* (2006.01)

(52) U.S. Cl. ................. 424/94.6; 424/94.63; 424/94.66; 424/439

(58) Field of Classification Search .................. None
See application file for complete search history.

(56) References Cited

U.S. PATENT DOCUMENTS

| | | | |
|---|---|---|---|
| 3,898,130 A | 8/1975 | Komatsu | |
| 3,995,066 A | 11/1976 | Muys et al. | |
| 4,056,442 A | 11/1977 | Huang et al. | |
| 4,245,041 A | 1/1981 | Denney | |
| 4,251,519 A | 2/1981 | Robbins et al. | |
| 4,259,440 A | 3/1981 | Gupta et al. | |
| 4,264,589 A | 4/1981 | Felts et al. | |
| 4,275,011 A | 6/1981 | Tanaka et al. | |
| 4,394,445 A | 7/1983 | Nix et al. | |
| 5,108,916 A | 4/1992 | Cobbs et al. | |
| 5,578,304 A | 11/1996 | Sipos | |
| 5,604,119 A | 2/1997 | Haraldsson et al. | |
| 5,759,543 A | 6/1998 | Morozova et al. | |
| 6,051,220 A | 4/2000 | Scharpe | |
| 6,660,508 B1 | 12/2003 | Cheung | |
| 6,699,496 B1 | 3/2004 | Kojima | |
| 7,056,720 B2 | 6/2006 | Jaye et al. | |
| 2002/0061302 A1 | 5/2002 | Sander-Struckmeier et al. | |
| 2004/0253257 A1 | 12/2004 | Cheung | |
| 2005/0249783 A1 | 11/2005 | Perez-Camargo et al. | |
| 2005/0250817 A1 | 11/2005 | Shlieout et al. | |
| 2006/0084153 A1 | 4/2006 | Bao et al. | |
| 2006/0121017 A1 | 6/2006 | Margolin et al. | |
| 2007/0202566 A1 | 8/2007 | Bornscheuer et al. | |
| 2008/0199448 A1 | 8/2008 | Ross et al. | |
| 2008/0213241 A1 | 9/2008 | Davidson et al. | |
| 2008/0260709 A1 | 10/2008 | Sawada et al. | |
| 2008/0279839 A1 | 11/2008 | Schuler et al. | |
| 2009/0035293 A1 | 2/2009 | Svendsen | |
| 2009/0317371 A1 | 12/2009 | Arbab | |
| 2009/0324574 A1 | 12/2009 | Mathur et al. | |
| 2010/0034797 A1 | 2/2010 | Svendsen et al. | |
| 2010/0040592 A1 | 2/2010 | Margolin et al. | |
| 2010/0239559 A1 | 9/2010 | Freedman et al. | |
| 2010/0269989 A1 | 10/2010 | Wang et al. | |
| 2011/0052514 A1 | 3/2011 | Justen et al. | |
| 2011/0110910 A1 | 5/2011 | Svendsen et al. | |
| 2011/0158976 A1 | 6/2011 | Svendsen et al. | |
| 2011/0171294 A1 | 7/2011 | Edens et al. | |

FOREIGN PATENT DOCUMENTS

| | | |
|---|---|---|
| DE | 1 964 9097 | 5/1998 |
| EP | 0 387 945 | 9/1990 |
| GB | 1 546 328 | 3/1978 |
| GB | 1 084 431 | 5/1979 |
| WO | WO 91/18623 | 12/1991 |
| WO | WO 99/49877 A2 | 10/1999 |
| WO | WO 99/49877 A3 | 12/1999 |
| WO | WO 03/016518 | 2/2003 |
| WO | WO 2006/136159 | 12/2006 |
| WO | WO 2007/055735 | 5/2007 |
| WO | WO 2008/028300 | 3/2008 |
| WO | WO 2010/020693 | 2/2010 |
| WO | WO 2010/025126 | 3/2010 |
| WO | WO 2010/085975 | 8/2010 |
| WO | WO 2010/124387 | 11/2010 |

OTHER PUBLICATIONS

Haffner (ed) "Dyslipidemia Management in Adults With Diabetes", Diabetes Care, 2004, vol. 27, supp. 1, pp. S68-S71.*
Berndt (1980) "Influence of High Doses of Lipase from *Candida cylindracea* on the Serum Parameter for Normal Persons," Med. World (31)4: 148.
Antonios et al. (2008) *European Neurology* 60(6): 269-278 [Abstract Only].
Breuer (2001) *Current Medical Research Opinion* 17(1): 60-73 [Abstract Only].
Chen et al. (2008) *International Journal of Obesity* 32(11): 1694-1704.
Du et al. (2001) *Human Molecular Genetics* 10(16): 1639-1648.
Haemmerle et al. (2002) *Journal of Biological Chemistry* 277(7): 4806-4815.
Johansen (2011) *Current Opinion in Lipidology* 22(4): 247-253 [Abstract Only].
Keung et al. (1999) *Southern Medical Journal* 92(9): 912-914 [Abstract Only].
Layer et al. (2003) *Pancreas* 26(1): 1-7.

(Continued)

*Primary Examiner* — Jeffrey S. Lundgren
*Assistant Examiner* — Stephanie Springer
(74) *Attorney, Agent, or Firm* — Hunton & Williams LLP (57) ABSTRACT

The invention relates to methods and compositions for reducing serum levels of triacylglycerides in human subjects. In particular, the invention relates to the oral administration of an effective amount of a fungal lipase formulation, to a human subject having borderline-high or high serum levels of triacylglycerides, for a time period sufficient to reduce serum triacylglyceride levels.

20 Claims, 9 Drawing Sheets

OTHER PUBLICATIONS

Levy et al. (1995) *The FASEB Journal* 9: 626-635.
Mansbach et al. (1982) *Journal of Lipid Research* 23:1009-1019.
Milionis et al. (2001) *Diabetes and Metabolism* 27(2 Part 1): 160-163 [Abstract Only].
Phan et al. (2001) *Frontiers in Bioscience* 6: 299-319.
Stroes et al. (2008) *Arteriosclerosis, Thrombosis, and Vascular Biology* 28(12): 2304-2304.
Van De Woestijne et al. (2011) *Obesity Reviews* 12(10)829-840 [Abstract Only].
Wang et al. (2000) *Journal of Agricultural and Food Chemistry* 48(8): 3183-3189.
Yang et al. (1991) *Journal of Lipid Research* 32: 1173-1186.
Yeaman (2004) *Biochemical Journal* 379(Part 1): 11-22.
European Patent Office Machine Translation of FR 2 362 863, listed at Cite No. 39, 1978.

* cited by examiner

METHOD AND COMPOSITIONS TO REDUCE SERUM LEVELS OF TRIACYLGLYCERIDES IN HUMAN BEINGS USING A FUNGAL LIPASE

BACKGROUND OF THE INVENTION

1. Field of the Invention

The invention relates to methods and compositions for reducing serum levels of triacylglycerides in human subjects. In particular, the invention relates to the oral administration of an effective amount of a fungal lipase formulation, to a human subject having high or borderline-high serum levels of triacylglycerides, for a time period sufficient to reduce serum triacylglyceride levels.

2. Description of Related Art

Triacylglyceride Levels

A recent study by Ford et al. (Arch Intern Med, 169(6): 572-578, 2009), at the Centers for Disease Control (CDC), involving 5,610 participants, showed that 33.1 percent of the participants had serum triacylglyceride levels defined as borderline high (>150 milligrams per deciliter). Nearly 18 percent had serum triacylglyceride levels defined as high (>200 milligrams per deciliter). High triacylglyceride levels may lead to atherosclerosis, which can increase the risk of heart attack and stroke. Persons with high triacylglyceride levels often have additional conditions that can increase their chances of developing heart disease, such as obesity and diabetes.

Hypertriglyceridemia is a human condition characterized by the presence of high serum levels of triacylglycerides. It has been associated with obesity, but can also be induced by other factors, independent of overall body fat (C T Johansen and R A Hegele, Curr. Opin. Lipidol., 22(4):247-253, 2011). The presence of single nucleotide polymorphisms in cellular genes such APOA5, APOB, GCKR, and LPL can induce severe hypertriglyceridemia in human beings. It is thought that more than 20% of the susceptibility to hypertriglyceridemia is caused by genetic mutations. Endothelial cell dysfunction and adipose cell dysfunction can lead to hypertriglyceridemia (H W Breuer Curr. Med. Res. Opin. 17(1):60-73, 2001; A P van de Woestijne et. al. Obes. Rev. 10.1111 (epub ahead of print) Jul. 12, 2011. Hypertriglyceridemia can be induced by specific drugs. For example, interferon alfa-2b and asparaginase have been shown to induce hypertriglyceridemia by two unique biochemical mechanisms (Y K Keung et. al. South. Med. J. 92(9):912-914, 1999). Taken together, these studies indicate that high serum levels of triacylglycerides can be induced in human beings by multiple factors independent of obesity.

High serum levels of triacylglycerides (commonly called triglycerides; also referred to herein as "TAG") have been identified as one of several lipid abnormalities commonly associated with patients that have type 2 diabetes (Bitzur et al., Diabetes Care 32 (suppl 2): S373-S377, 2009). It is currently unknown what mechanism(s) causes elevated serum TAG levels in these patients. The effect could be multi-factorial in nature, with contributions by diminished suppressive effects of insulin action, impaired clearance of lipid particles containing TAG, and the conscious dietary decisions by patients with type 2 diabetes to reduce carbohydrate caloric intake, replacing it with more meat and fats in their diets. Several prospective studies have identified hypertriglyceridemia as an independent predictor of type 2 diabetes. Recently, profiling of TAG molecules has been employed to help predict those that will acquire type 2 diabetes in the future (Rhee et al. J. Clin. Invest. 121(4):1402-1411, 2011).

In view of these studies, clinicians monitor the level of triglycerides in a patient's serum, and researchers are looking for methods of lowering serum triglyceride levels.

Lipases

Lipases are enzymes that the body uses to break down fats to aid in the digestion of food. The specificity of lipases is derived from the molecular properties of the lipase, the structure of a potential substrate, and factors that affect the binding of the lipase to a substrate (Jensen R G et al. Lipids, 18(3): 239-252, 1983). One of the most important lipases in the human body is pancreatic lipase. Pancreatic lipase breaks down triacylglycerides from ingested fats into smaller components that can be readily absorbed by intestinal cells (i.e., enterocytes), such as free fatty acids (FA) and 2-monoacylglyceride (2-MAG) (Pham, C. T. and Tso, P., Frontiers in Bioscience 6:d299-319, 2001; Levy et al. FASEB J. 9:626-635, 1995). The enterocyte synthesizes the FA and 2-MAG components into triacylglycerides (TAG) primarily via the Monoacylglyceride Pathway. The newly synthesized TAG are packaged into chylomicrons and then exocytosed into intracellular spaces and nearly lymphatic vessels. Chylomicrons containing TAG are ultimately distributed throughout the body for energy production and synthetic processes.

Historically, attempts to enhance/supplement lipid digestion have focused on oral administration of supplemental amounts of pancreatic lipase. However, naturally supplied pancreatic lipase is secreted directly into the intestine via the bile duct, while oral supplements must first transit the stomach. Pancreatic lipase is not stable in the acidic environment of the stomach whether it is empty (pH 1-2) or full (pH 3-4), and rapidly loses its enzymatic activity during exposure to these low pH conditions. Previous attempts to overcome the instability of pancreatic lipase activity at acid pH have shown unsatisfactory results. Approaches have included using enteric-coated tablets of pancreatic lipase (Graham D Y, New England Journal of Medicine 296:1314-1317, 1977), microsphere-encapsulated pancreatic lipase (see U.S. Pat. Nos. 5,260,074; 5,324,514; 5,352,460; 5,405,621), and cross-linked lipase crystals (see U.S. Patent Applications 2001/0046493 and 2003/0017144).

Accordingly, there remains a need for a lipase formulation that can be easily ingested and exert effective lipase activity, first in the acid pH environment of the full stomach and then in the neutral pH environment of the intestine.

SUMMARY OF THE INVENTION

The present invention provides lipase formulations that are stable and active in acidic and neutral pH environments, and that also break down dietary fats such as triacylglycerides into fatty acids (FA) and glycerol. By fully digesting triacylglycerides to FA and glycerol, which is beyond the scope of pancreatic lipase digestion, the lipase formulations of the invention enhance lipid digestion. The inventors have determined that these lipase formulations can significantly lower serum triacylglyceride levels in human beings.

As such, the invention provides improved lipase compositions useful in treating human beings with high and borderline-high serum levels of triacylglycerides, as well as methods of reducing serum triacylglyceride levels in humans by administering these compositions.

In particular, the invention provides for methods of reducing serum triacylglyceride levels in a human subject by administering a composition comprising an effective amount of a fungal lipase that (i) exhibits at least 50% of its maximum activity over the pH range of 2.0 to 8.0; and (ii) cleaves all three ester sites of a triglyceride, to a human subject in need thereof.

In one embodiment, the method involves administering the composition periodically and over a time period sufficient to reduce serum triacylglycerides by at least 20% compared to the serum triacylglycerides of the human subject before administering the composition to the human. For example, the composition may be administered at each meal, or a majority of meals, for at least a week or a month.

In another embodiment, the method reduces serum triacylglycerides in a human subject having at least 150 mg/dL of serum triacylglycerides. In another embodiment, the human subject is at risk for or has diabetes.

In particular embodiments, the effective amount of the lipase may be, for example, at least 15,000 FIP units/meal, at least 180,000 FIP units per gram of protein, or at least 2000 FIP units per gram of fat consumed by said human subject. Suitable fungal lipase may be a lipases derived from the Candida family such as a Candida rugosa (also known as Candida cylindracea) or Candida antarctica lipase.

BRIEF DESCRIPTION OF THE DRAWINGS

FIG. 4 contains two graphs showing the effect of pH on the activity (FIG. 4A) and stability (FIG. 4B) of the lipase preparation derived from Candida rugosa.

FIG. 5 contains four graphs showing the effect of pH on the enzymatic activity (FIG. 5A) and stability (FIG. 5B) of the lipase preparation derived from Aspergillus niger, and the effect of pH on the enzymatic activity (FIG. 5C) and stability (FIG. 5D) of the lipase preparation derived from Rhizopus oryzae. The lipases were analyzed as described for FIGS. 4A and 4B.

DETAILED DESCRIPTION OF PREFERRED EMBODIMENTS OF THE INVENTION

The invention provides improved enzyme compositions and methods for treatment of human beings with higher than normal serum levels of triacylglycerides. In particular, the invention provides for the administration of lipases that are (1) active and stable throughout the digestion (i.e., active and stable in acidic, acidic-to-neutral, and neutral pH); and (2) will hydrolyze all three fatty acid bonds of a triacylglyceride, in amounts effective to reduce serum levels of triacylglycerides. The invention provides effective amounts of the lipase compositions, and it directs these compositions at human populations that will benefit from their administration.

Lipase Activity and Stability

The invention provides for the use of lipases that are active and stable in the acid environment of stomach and can begin digestion of dietary triacylglycerides there. The lipases are also active and stable in acidic-to-neutral pH and neutral pH conditions. As such, the lipases are active and stable throughout digestion. Examples of such lipases include lipases from the Candida family (e.g., C. rugosa and C. antarctica). In one embodiment, the lipase exhibits at least 50% of its maximum activity over the pH range of 2.0 to 8.0. It will be understood that other activity and stability ranges may be derived from, and are supported in, the Figures herein or from U.S. Publication No. 2008/0279839, which is hereby incorporated by reference.

Cleavage Activity of Lipase

The lipases used in the compositions and methods of the invention are capable of cleaving all three ester sites (sn-1, sn-2, and sn-3) of triacylglycerides. The lipases can cleave fatty acid components off of the TAG at these three sites whether they are short, medium, or long in length, and/or whether they are unsaturated or saturated.

Figure 1:
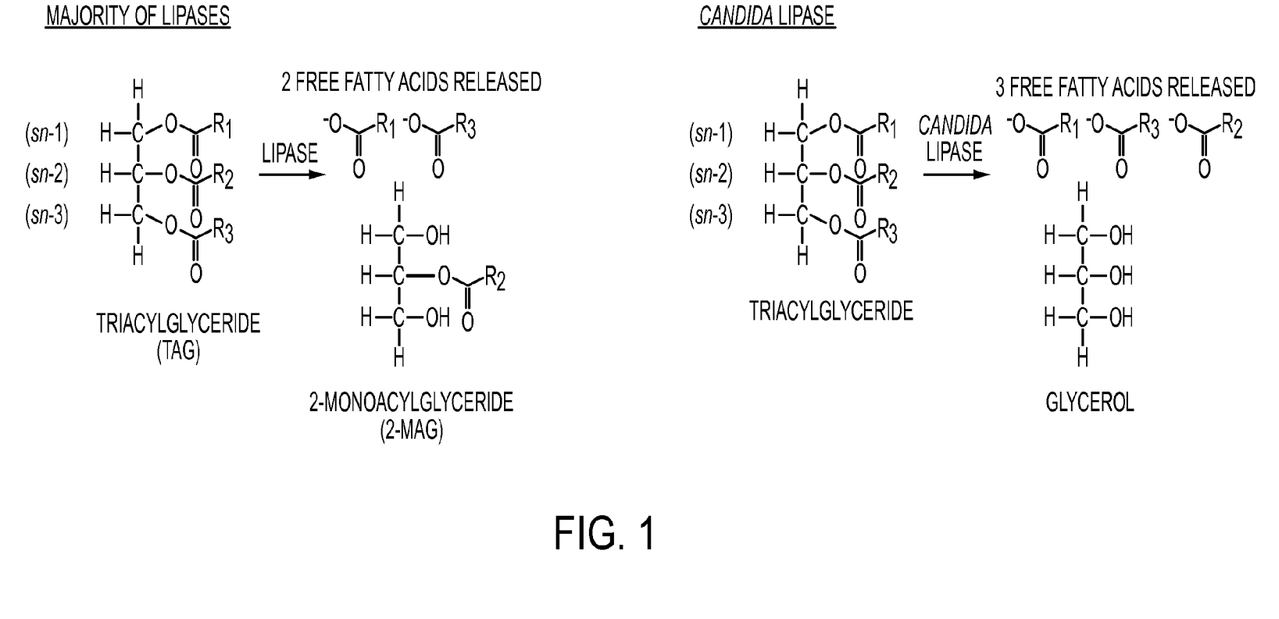
FIG. 1 is a two-part diagram comparing the enzymatic actions of lipases having 1,3-specificity on triacylglycerides, and the actions of non-specific lipases on triacylglycerides.

It is understood that most lipases only cleave the sn-1 and/or sn-3 external sites of triacylglycerides and are unable to cleave all three ester sites. This results in the generation of up to two free fatty acid molecules and 2-monoacylglyceride (2-MAG) from triacylglyceride catabolism by these lipases, i.e., these lipases incompletely digest triacylglycerides. See FIG. 1, first panel. In contrast, preferred lipases of this invention, such as those derived from Candida rugosa and Candida antarctica, are able to fully digest triacylglycerides to three free fatty acid molecules and a glycerol backbone. See FIG. 1, second panel.

One study characterized the substrate specificity of 25 lipases from numerous sources and found only 6 lipases (mainly Candida and Geotrichum lipases) that showed reactivity towards the sn-2 region of triacylglycerides (Rogalska et al., Chirality, 5:24-30, 1993). Nearly all of the sn-2 position-reactive lipases analyzed preferred to hydrolyze the external sn-1 and sn-3 positions, rather the internal sn-2 position of triacylglycerides, except for the Candida antarctica lipase, which showed a slight preference for the sn-2 position. Some of the sn-2 position-reactive lipases were derived from *Geotrichum* species.

Recent work has indicated that some *Geotrichum*-derived lipases are stable within a pH range of 6.5-8.0 (e.g., Gopinath S. C. B., et al World J Review of MICB and Biotechnol., 19(7):681-689, 2003) suggesting that these particular lipases may be poorly effective in the acidic pH of the stomach for triacylglyceride digestion. *Geotrichum*-derived lipases that are stable at acidic pH, however, may be helpful and show some benefit at achieving improved digestion of triacylglycerides. Other microbial lipases, such as the one derived from *Aspergillus niger*, are stable at acidic pH, but will only attack the sn-1 and sn-3 positions of triacylglycerides, and also exhibit much greater substrate restriction than the more substrate-promiscuous *Candida rugosa* lipase, the preferred lipase of the invention. Accordingly, the invention contemplates the use of lipases, other than those derived from the *Candida* family, that cleave all three ester sites (sn-1, sn-2, and sn-3) of triacylglyceride.

Non-Binding Mechanistic Theory

The human body, through pancreatic lipase, breaks down triacylglycerides from ingested fats into free fatty acids (FA) and 2-monoacylglyceride (2-MAG). Intestinal enterocytes synthesize the FA and 2-MAG components into triacylglycerides primarily via the Monoacylglyceride Pathway. TAG are ultimately distributed throughout the body for energy production and synthetic processes.

Figure 2:
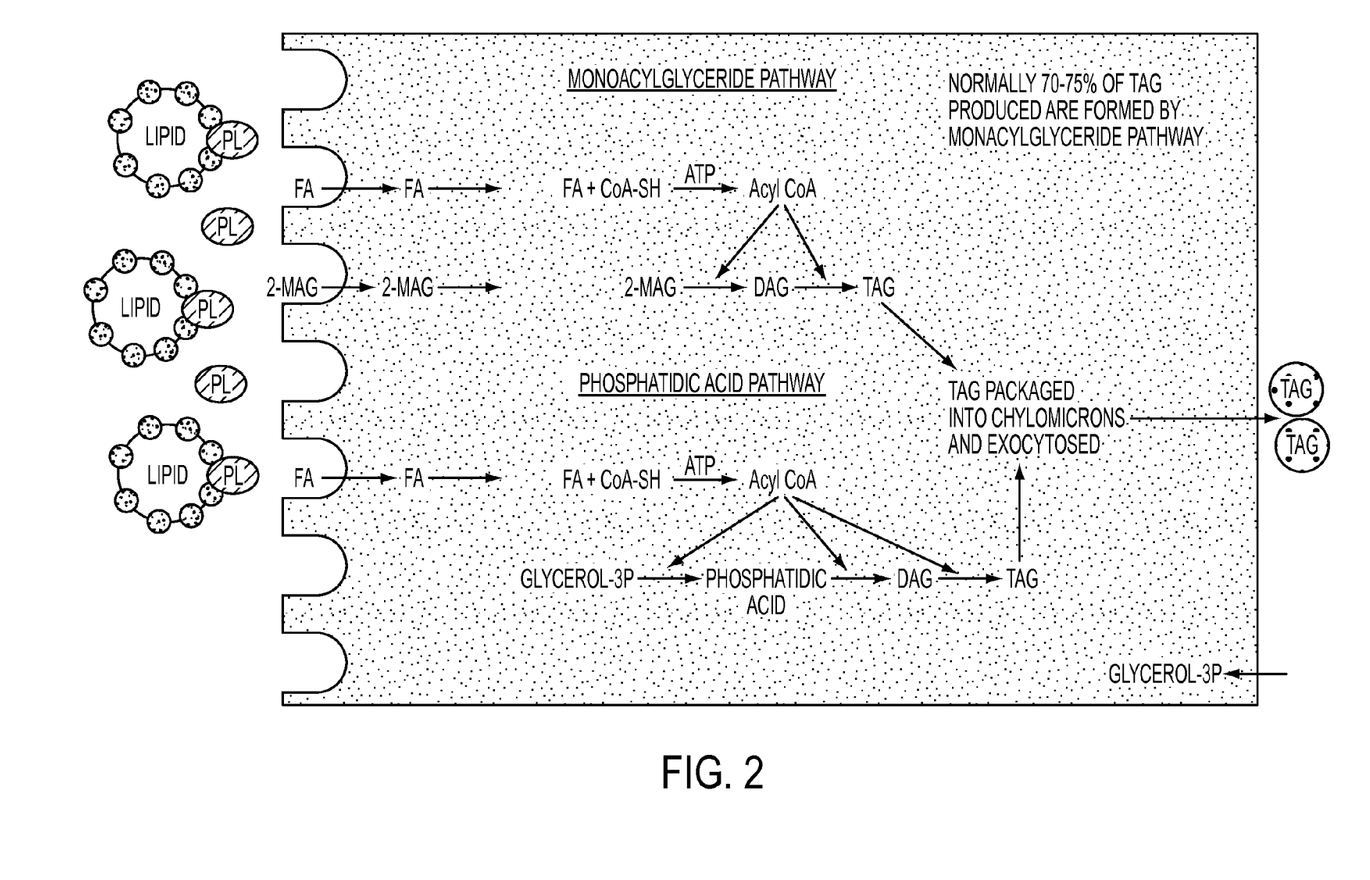
FIG. 2 is a drawing showing the normal absorption of lipids by enterocytes and synthesis of triacylglycerides. Figure Abbreviations: Pancreatic Lipase (PL); Free Fatty Acid (FA); 2-Monoacylglyceride (2-MAG); Diacylglyceride (DAG); Triacylglyceride (TAG); Coenzyme A (CoA); Glycerol 3-Phosphate (Glycerol-3P).

FIG. 2 depicts the normal digestion of lipid mixed micelles by pancreatic lipase. During the normal digestive process, mixed micelles are formed by the combination of bile salts with triacylglycerides to increase solubility of the lipid components. In the intestinal lumen, pancreatic lipase (PL) is assisted in anchoring to these mixed micelles by the action of colipase, an accessory protein secreted by the pancreas. Pancreatic lipase digests the triacylglycerides contained in mixed micelles to fatty acids (FA) and 2-monoacylglyceride (2-MAG). These two digestion products (FA and 2-MAG) are quickly absorbed by the enterocyte and primarily shuttled to the Monoacylglyceride Pathway for reformation into TAG.

Some studies have shown that 2-MAG can isomerize to the 1-monacylglyceride conformation in vitro. This phenomenon is not thought to be physiologically significant because absorption of 2-MAG by the enterocyte is too rapid for the isomerization process to occur. Normally, 70-75% of triacylglycerides produced by the enterocyte are synthesized via the Monoacylglyceride Pathway in the smooth endoplasmic reticulum (Mansbach and Parthasarathy, J. Lipid Research, 23:1009-1019, 1982; Levy et al. FASEB J, 9:626-635, 1995). After subsequent addition of apoproteins and other components, TAG-rich pre-chylomicrons are transported towards the basolateral region of the enterocyte and exocytosed into the extracellular space where the mature chylomicrons make their way to the lymphatics and are distributed throughout the body.

A second TAG-synthetic pathway is also active in enterocytes. The Phosphatidic Acid Pathway synthesizes far smaller amounts of TAG compared to the Monoacylglyceride Pathway, mainly because it is constrained by the scarceness of its key pathway substrate, glycerol 3-phosphate (glycerol-3P). Glycerol-3 phosphate is usually imported by the enterocyte from other sources, such as from hepatic production. It has been shown that both the Monoacylglyceride Pathway and Phosphatidic Acid Pathway converge at the smooth endoplasmic reticulum and produce essentially identical TAG-rich chylomicron particles for export (Yang, L.-Y. and Kuksis, A., J. Lipid Research 32:1173-1186, 1991).

Figure 3:
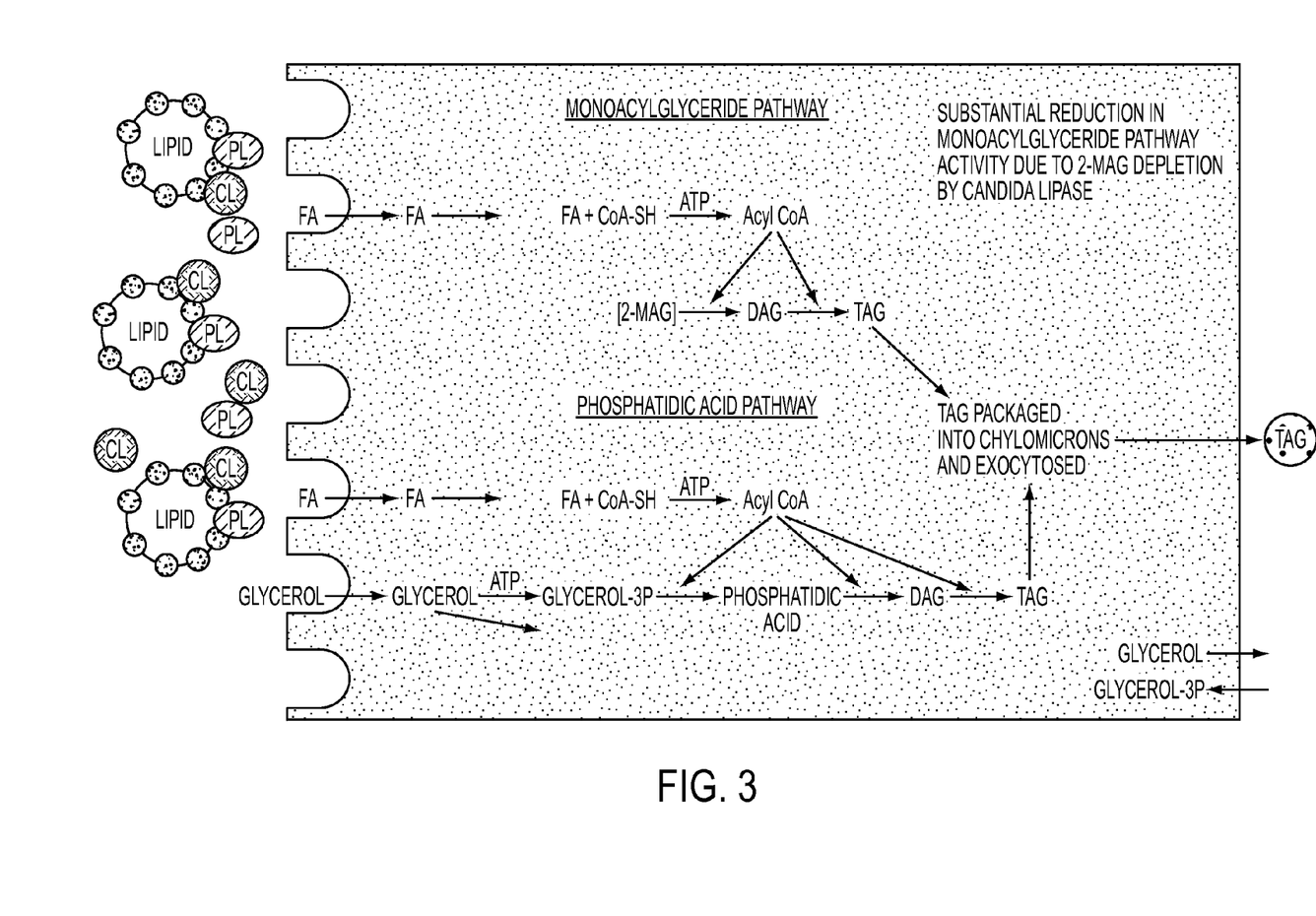
FIG. 3 is a drawing showing the effects of Candida rugosa lipase on absorption of lipids by enterocytes and synthesis of triacylglycerides. Figure Abbreviations: Pancreatic Lipase (PL); Candida Lipase (CL); Free Fatty Acid (FA); Significantly Reduced Levels of 2-Monoacylglyceride [2-MAG]; Diacylglyceride (DAG); Triacylglyceride (TAG); Coenzyme A (CoA); Glycerol 3-Phosphate (Glycerol-3P).

Without wishing to be bound, the inventors theorize that the lipase compositions described herein reduce the serum levels of triacylglycerides, by the concerted actions of the lipase (e.g., *Candida* lipase) and native pancreatic lipase on dietary lipids in vivo. By working together, the lipases are better able to completely digest most dietary triacylglycerides to three molecules of fatty acids and one molecule of glycerol. A suggested scenario of the biochemical events involved is shown in FIG. 3.

During the enhanced digestive process, pancreatic lipase (PL) and *Candida* lipase (CL) digest triacylglycerides contained in mixed micelles to fatty acids (FA) and 2-monoacylglyceride (2-MAG). *Candida* lipase can then further digest the 2-MAG product into an additional FA molecule and free glycerol molecule. These two digestion products (FA and glycerol) are quickly absorbed by the intestinal enterocyte. The complete digestion of TAG causes a substantial decrease in the activity of the Monoacylglyceride Pathway since its substrate; 2-MAG has been greatly depleted. It has been shown in a previous study that the Phosphatidic Acid Pathway can become the major synthetic route of TAG production in the absence of 2-MAG (Mansbach and Parthasarathy, 1982). This synthetic compensation depends on the availability of the pathway substrate, glycerol-3 phosphate. Enterocyte glycerol kinase activity can produce the Phosphatidic Acid Pathway's substrate, glycerol-3 phosphate (glycerol-3P). The activity of glycerol kinase in the enterocyte, however, has been shown to be limited and most glycerol is believed to flow through and out the enterocyte to be used by other cellular synthetic pathways in the body. Most glycerol-3 phosphate is thought to be imported into the enterocyte from other sources. Thus, the concerted actions of native pancreatic lipase and *Candida* lipase on dietary lipids may lead to reduced amounts of triacylglycerides being synthesized and packaged into chylomicrons by intestinal enterocytes for extracellular transport, where such TAG-rich particles may end up ultimately contributing to serum levels of triacylglycerides in human beings.

It is believed that the broadly-reactive lipase formulations of the invention deplete the 2-MAG component critical for the synthesis of new triacylglycerides by intestinal enterocytes which use the Monoacylglyceride Pathway. As a result, the lipase formulations of the invention reduce the levels of serum triacylglycerides.

Administration of Lipase Formulations

The invention provides for administering an effective amount of the lipase formulations of the invention. The effective amount may include, for example, compositions comprising certain levels of lipase activity (measured in FIP units), or lipase amounts such that, when the lipase is administered for sufficient time period, serum TAG levels are reduced compared to serum TAG levels before administration the compositions.

In one embodiment, the effective amount of the lipase comprises at least 15,000 FIP units per meal, which may be delivered by one or more capsules or tablets. For example, the effective amount may be at least 25,000, 40,000, 50,000, 70,000, 90,000, 100,000, 125,000, 150,000, 175,000, 200,000, 225,000, or 250,000 FIP units, which may be delivered by one or more capsules or tablets. It will be understood that the invention contemplates ranges of these effective amounts (e.g., 15,000 to 250,000 FIP units per meal, capsule or tablet).

In another embodiment, the effective amount of the lipase comprises at least 2000 FIP units per gram of fat consumed by a human subject. For example, the enzyme's activity may be at least 2250, 2500, 3000, 3500, 4000, 4500, or 5000 FIP units per gram of fat consumed by a human subject. It will be understood that the invention contemplates ranges of these effective amounts (e.g., 2,000 to 5,000 FIP units per gram of fat consumed by a human subject).

In another embodiment, the enzyme in the lipase composition of this invention comprises at least 180,000 FIP units per gram of the lipase. For example, the enzyme's activity may be at least 200,000, 225,000, 250,000, 300,000, 350,000, 375,000, 400,000, 450,000, or 500,000 FIP units per gram of the lipase. It will be understood that the invention contemplates ranges of these amounts (e.g., 180,000 to 500,000 FIP units per gram of the lipase).

In another embodiment, the lipase may comprise at least 2, 5, 10, 20, 30, 40, 50, 60, 70, 80, 90, 95, or 100% of the dosage weight. It will be understood that the invention contemplates ranges of these amounts (e.g., the lipase may comprise 2 to 100% of the capsule or tablet weight). The remainder of the dosage may be any combination of known pharmaceutical excipients, so long as the excipients do not unduly degrade the stability of the lipase during storage.

The lipase formulations of the invention are administered for a time period sufficient to reduce serum TAG levels compared to the serum TAG levels of the human subject to whom the lipase compositions of the invention had not been administered. For example, the lipase compositions may be administered over a time period sufficient to reduce serum triacylglycerides by at least 20, 25, 30, 35, 40, or 50% compared to the serum triacylglyceride level of the human subject before administering the composition to said human. In preferred embodiments, the period of chronic administration sufficient to reduce serum triacylglycerides by these levels may be for at least one, two, three, or four weeks (one month). In other embodiments, the compositions of the invention may be administered for longer periods of time such as two, four, six, nine, or twelve months. In yet another embodiment, the compositions of the invention may be administered as part of a daily regimen (e.g., administered with meals) for many years or the remainder of the subject's life.

Typically, the lipase formulations of the invention are administered with food (e.g., with each meal) at the time the food (e.g., meal) is consumed. Alternatively, the lipase formulations may be administered "substantially contemporaneously with food." As used herein, "substantially contemporaneously with food" means that the lipase formulations are administered before or after ingestion of food (e.g., a meal) and preferably within 5, 10, 15, 20, 25, 30, 35, 40, 45, 50, 55, or 60 minutes before or after ingesting food (e.g., a meal).

The lipase dosages of the invention are typically administered in the form of capsules or tablets. In a preferred embodiment, the lipase formulation is administered in a single capsule or tablet. In another embodiment, the lipase formulation is administered using multiple capsules or tablets. Exemplary capsule or tablets may be 200-500 mg.

Human Populations

The invention provides for methods of administering the lipase formulations to human subjects having elevated TAG levels. In one embodiment, the human subject has above normal TAG levels (at least 150 mg/dL). In another embodiment, the human subject has borderline high TAG levels (150-199 mg/dL), high TAG levels (200-499 mg/dL), or very high TAG levels (2500 mg/dL).

The invention provides for methods of administering the lipase formulations to human subjects having diseases or conditions associated with elevated TAG levels. In one embodiment, the human subject is at risk for or has diabetes. In another embodiment, the human subject has diabetes and is compensating for low carbohydrate caloric intake with higher fat and protein intake. In another embodiment, the human subject is at risk for or has type 2 diabetes (e.g., the human subject has type 2 diabetes and is at risk for coronary disease).

Combinations of Various Embodiments and Concepts

It will be understood that the embodiments and concepts described herein may be used in combination. For example, the invention provides for a method of reducing serum triacylglyercide levels in a human subject comprising administering a composition comprising an effective amount of a fungal lipase, wherein (i) the fungal lipase is from *C. cylindracea*; (ii) the effective amount of *C. rugosa* (*cylindracea*) is at least 15,000 FIP units/meal; (iii) the composition is administered over a time period sufficient to reduce serum triacylglycerides by at least 20% compared to the serum triacylglycerides of the human subject before administering the composition to said human; and (iv) said human subject has at least 150 mg/dL of serum triacylglycerides before administering the composition. Accordingly, other combinations of lipases, effective amounts, modes of administrations, and patient populations are also envisioned.

EXAMPLES

The following examples are not intended to limit the invention in any way.

Example 1

Activity and Stable of Lipases

Figure 4A:
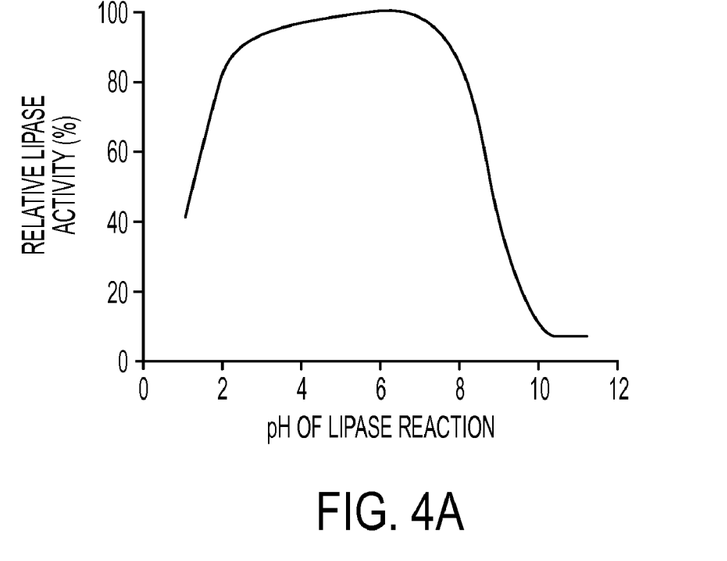
Figure 4B:
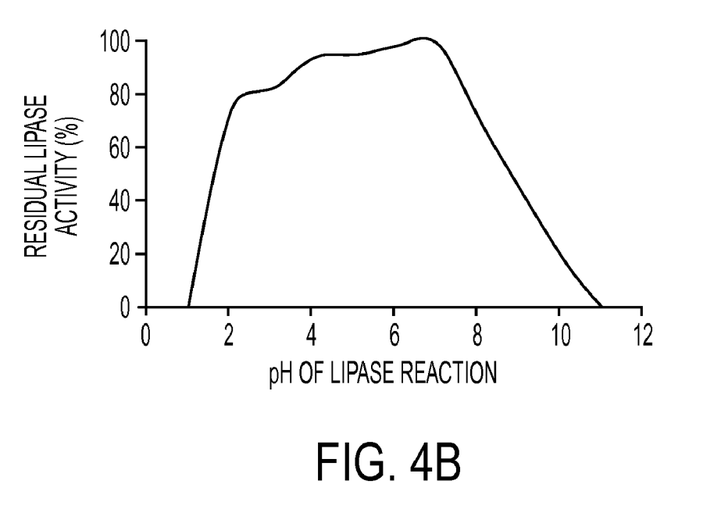

FIGS. 4A and 4B show the effect of pH on the enzymatic activity (FIG. 4A) and stability (FIG. 4B) of *Candida rugosa* lipase. A Fungal Lipase International (FIP) activity assay (Food Chemical Codex protocol, Volume 7: 1201-1202, 2011) was used to determine that the *Candida rugosa* lipase is fully active in a pH range of 2-8, and preferably a pH range of 3-8. An FIP unit is the amount of enzyme required to release one micromole of fatty acid from triglyceride in one minute. The standard FIP assay uses an automatic pH titration instrument to maintain the neutral pH of the lipase reaction mixture (pH 7); the temperature is 37° C. As fatty acids are released by the lipase from the olive oil substrate, the pH drops and 0.02N NaOH solution is automatically added to the reaction mixture maintain the neutral pH. The measurement of the exact volume of the NaOH solution used to maintain a neutral pH during the reaction can be employed to calculate lipase activity.

For the pH effects graph shown in FIG. 4A, the automatic titration instrument was set to maintain the reaction at the different pH levels shown in the graph. The results indicate that *Candida rugosa* lipase is fully active at pH 3-4; a similar pH achieved by the nearly full stomach. The *Candida rugosa* lipase is stable at low pH and retains the majority of its enzymatic activity (FIG. 4B). For these experiments, *Candida rugosa* lipase was pre-incubated in appropriate buffers at different pH levels for 2 hours at 37° C. before performing the FIP activity assay (pH 7.0). Taken together, the data indicates that *Candida* lipase can begin breakdown of triacylglycerides in the full stomach.

Figure 5A:
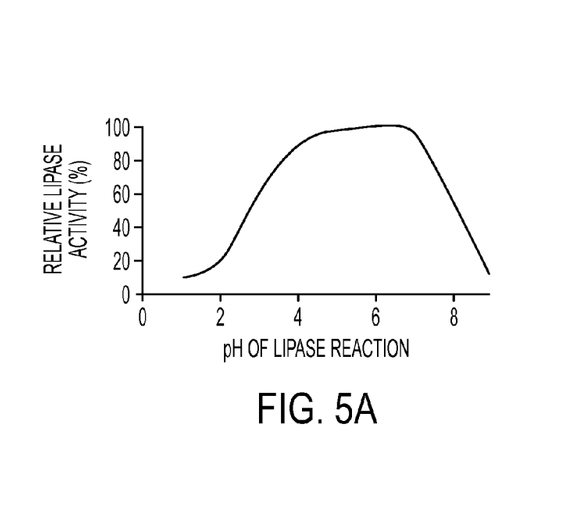
Figure 5B:
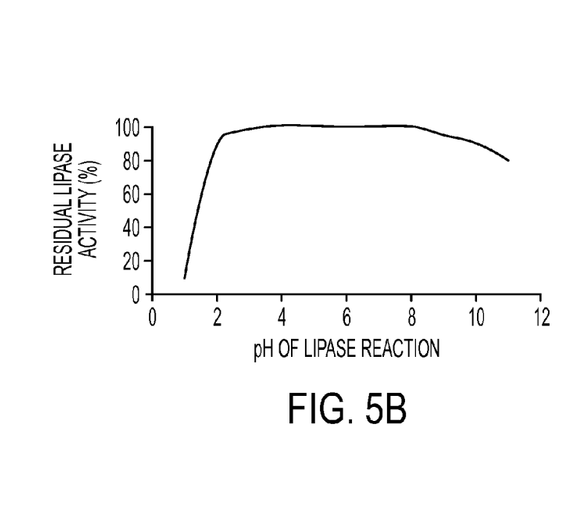
Figure 5C:
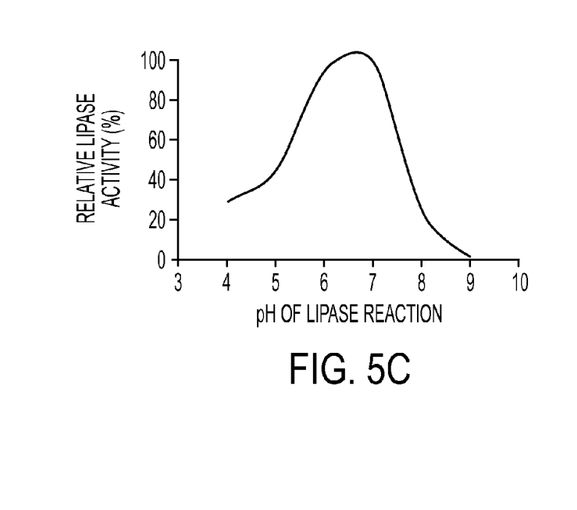
Figure 5D:
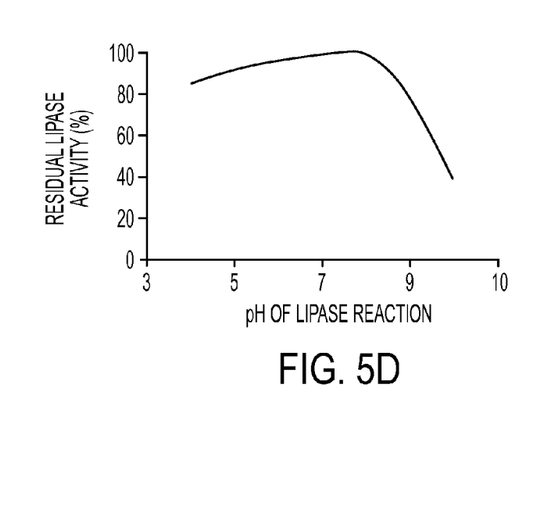

The effects of pH on the enzymatic activities and stabilities of two other microbial lipases are shown in FIGS. 5A-5D. The effect of pH on the enzymatic activity and stability of *Aspergillus niger* lipase is shown in FIGS. 5A and 5B, respectively. The lipase derived from *Aspergillus niger* demonstrated slightly less relative enzymatic activity at low pH compared to the *Candida rugosa* lipase, but shows similar consistent enzyme stability over a wide pH range. The effect of pH on the enzymatic activity and stability of *Rhizopus oryzae* lipase is shown in FIGS. 5C and 5D, respectively. The lipase derived from *Rhizopus oryzae* demonstrated significantly less relative enzymatic activity at low pH compared to the *Candida rugosa* lipase, and also shows less enzyme stability over a narrower pH range.

Digestion of Triacylglycerides Using Lipase Formulations (Examples 2-5)

The inventors preformed hydrolysis experiments using various lipases at pH 4 and 7, and measured the amount of glycerol, if any, released from triacylglycerides by the lipases.

Hydrolysis Experiments

The experiments tested the hydrolysis of triacylglyceride oils (soybean and olive oil) using the following lipases: pig pancreas lipase (American Labs Inc., Omaha Nebr.), *Aspergillus niger* lipase (Bio-Cat Inc., Troy Va.), *Rhizopus oryzae* lipase (Bio-Cat Inc.), and *Candida rugosa* lipase (Bio-Cat Inc.).

A standard reaction protocol was used to assess triacylglyceride digestion by different lipases. The lipase reactions were performed using a 100 ml jacketed beaker, kept at 37° C. by using a Fisher Isotemp recirculating water bath. 5 mL of 0.05M $CaCl_2$ and 1 mL of 5 mg/mL bile salts were added to the pre-warmed jacketed beaker. The reaction mixture beaker was slowly stirred using a stir bar on a magnetic stir plate. For most experiments (results shown in FIGS. 6, 7, and 9), 12,900 FIP units were used for hydrolysis (860 FIP Units per mL of oil). The lipases were weighed out on tarred weigh paper then transferred to a 20 mL tube using 4 mL water and vortexed until dissolved. The tube was rinsed twice with 4.25 mL of water, which was added to the reaction mixture. The reaction was brought to pH 4.0 (or 7.0 in some experiments) by the addition of 0.02N NaOH. The lipase reaction was started by the addition of 15 mL of soybean oil (FIGS. 6-8; Food Lion, Troy, Va.) or olive oil (FIG. 9; Sigma-Aldrich Chemicals, St. Louis, Mo.). Lipase reaction samples were obtained at 30, 60, 120 and 180 minutes and placed in microcentrifuge tubes. The samples were centrifuged for 5 minutes at 10,000 rpm to separate the oil and water layers and then stored at −20° C. in a freezer.

Triacylglyceride Digestion Analysis

Triacylglyceride digestion was quantitated by HPLC. For HPLC analysis, the oil layer was dissolved in acetone, the amount dependent on sample concentration. The HPLC system consisted of an Agilent 1100 series Degasser, Quaternary Pump, Autosampler, Column Oven, Refractive Index Detector and two Supelcosil LC-18 Columns (150×4.6 mm; Sigma-Aldrich) in series. The flow rate was 1 mL/min of Acetone/Acetonitrile (64:36, v/v) with the column oven set at 25° C. The Refractive Index Detector's Optical Temperature was set at 30° C. and peak width was set at >0.2 min. The triglyceride results were quantitated by using a modified version of the separation methods employed by Perkins (1979) and Podlanta and Töregård (1982), and as described in Supelco Bulletin 787D (Sigma-Aldrich 1997).

Example 2

Soybean Hydrolysis Results

Figure 6:
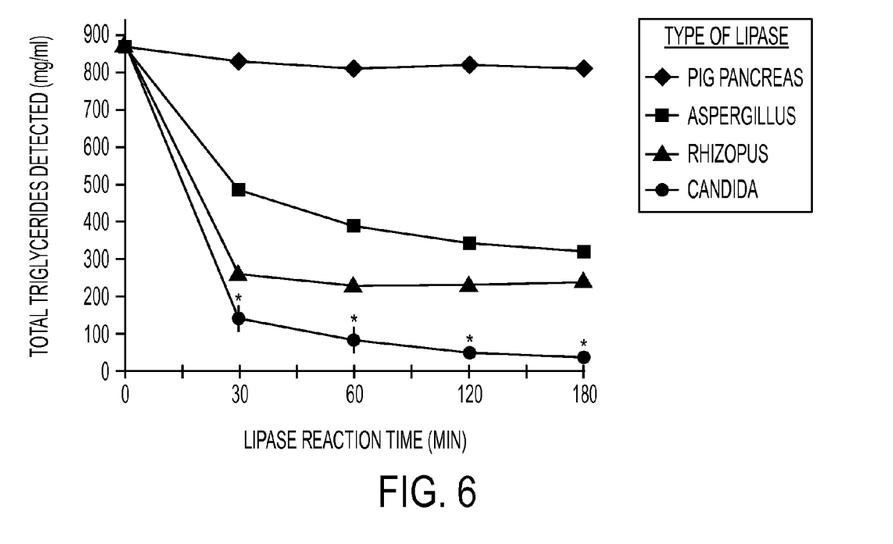
FIG. 6 is a graph comparing the temporal digestive effects of lipases from 4 sources (pig pancreas; Aspergillus niger, Rhizopus oryzae; and Candida rugosa) using soybean oil at pH 4. The effectiveness of action was measured by decreased HPLC detection of triacylglycerides following digestion into constitutive components (i.e., FA, 2-MAG, glycerol). In control preparations without lipase, an average of 874±8 mg/ml of triacylglycerides was detected at the four reaction time points studied.

FIG. 6 shows the results of the soybean oil hydrolysis at pH4. Compared to the other three lipases (n=4), *Candida* lipase (n=5) demonstrated significantly increased digestion of soybean oil triacylglycerides, at all four time points analyzed (*=P<0.01). Results were analyzed by a one-way ANOVA (P<0.01), followed by the post-hoc Tukey-Kramer HSD test, to determine significant differences between the lipase test groups. The standard error of the mean (SEM) bars are shown for the *Candida* lipase results. Similar results were found when the triacylglyceride reactions were performed at pH 7 (data not shown), except that pig pancreatic lipase showed a small amount of lipase activity at pH 7. It is unknown whether the pig pancreatic lipase preparation used contained colipase, the potential absence of which may have contributed to the results observed.

Example 3

Glycerol Analysis

A comparative temporal digestion of soybean oil triglycerides by four lipases (each containing 12,900 FIP Units) was performed using the standard reaction protocol (pH 4). Samples were prepared by dilution of aqueous layer in water; the oil layer was extracted in water (50:50, v/v) by vortexing for 30 seconds. The oil/water mix was then centrifuged at 10,000 rpm for 5 minutes. The water layer was diluted as needed using water. 1 mg/mL glycerol stock solution and all standards were prepared in water.

The amount of glycerol produced was quantitated by HPLC using a modified version of the separation method employed by Gandi et al. (The Application Notebook, Metrohm e-publication, LC_GC Chromatography online.com Dec. 2, 2009). The HPLC system consisted of an Agilent 1100 series Degasser, Quaternary Pump, Autosampler, Column Oven, Refractive Index Detector and Supelocgel C-610H Carbohydrate Column (300×7.8 mm: Sigma-Aldrich)). The flow rate was 0.5 mL/min of 0.1% phosphoric acid with the column oven set at 30° C. The Refractive Index Detector's Optical Temperature was set at 30° C. and peak width was set at >0.2 min.

Figure 7:
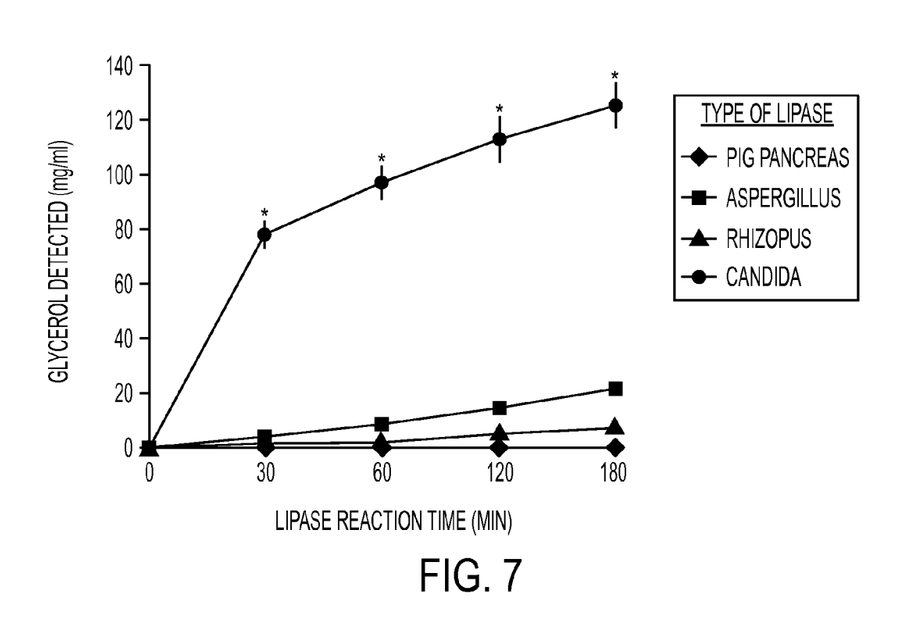
FIG. 7 is a graph comparing the temporal production of glycerol by lipases of four sources (pig pancreas; Aspergillus; Rhizopus; and Candida rugosa) using soybean oil at pH 4. The effectiveness of action was measured by increased HPLC detection of glycerol following digestion of soybean oil. In control preparations without lipase, no glycerol was detected at the four reaction time points studied.

FIG. 7 shows the results of the glycerol analysis. Compared to the other three lipases employed (n=4), *Candida* lipase (n=5) demonstrated significantly increased production of glycerol from complete digestion of soybean oil triglycerides at all four time points analyzed (*=P<0.01). Results were analyzed by a one-way ANOVA (P<0.01), followed by the post-hoc Tukey-Kramer HSD test, to determine significant differences between the lipase test groups. The standard error of the mean (SEM) bars are shown for the *Candida* lipase results. Similar results were found when the triacylglyceride reactions were performed at pH 7 and the amount of glycerol generated was analyzed (data not shown), i.e., *Candida* lipase produced significantly more glycerol at both pH 4 and pH 7 than the other 4 lipases studied.

Example 4

Concentration-Response Experiment

Figure 8:
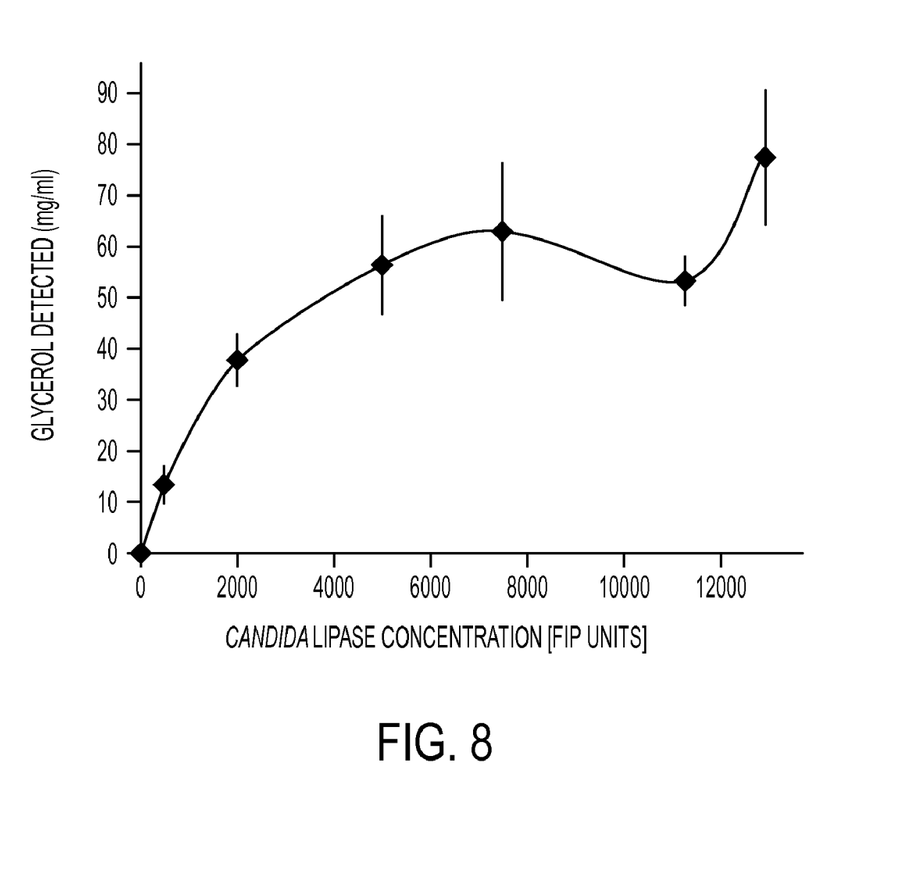
FIG. 8 is a concentration-response curve showing the specificity of the reaction by comparing increasing activity of the Candida rugosa lipase preparation to the production of glycerol. The Candida rugosa lipase needs to be used at an activity concentration capable of totally digesting TAG to FA and glycerol, and thus, achieve the invention's reductive effects in vivo on serum levels of TAG.

FIG. 8 shows concentration-response curves for *Candida* lipase. *Candida* lipase (500-12,900 FIP Units; 33.3-860 FIP Units per mL of oil) was reacted with soybean oil using the standard reaction protocol (pH 4) and the triacylglycerides were digested for 30 minutes. The amount of glycerol produced was quantitated by HPLC as described above. The amount of *Candida* lipase could be correlated with increased production of glycerol from complete digestion of soybean oil triglycerides, demonstrating the specificity of the reaction on glycerol production. The error bars depict the range of the amount of glycerol (duplicate to quadruplicate measurements) generated by the amount of *Candida* lipase used in the concentration response study.

Example 5

Olive Oil and Shortening Experiments

The inventors also tested whether the enhanced lipid digestive effects of *Candida* lipase on soybean oil triacylglycerides appears to be a general phenomenon applicable to action on other sources of triacylglycerides. As such, experiments were performed using olive oil and shortening as a source of triacylglycerides.

Figure 9:
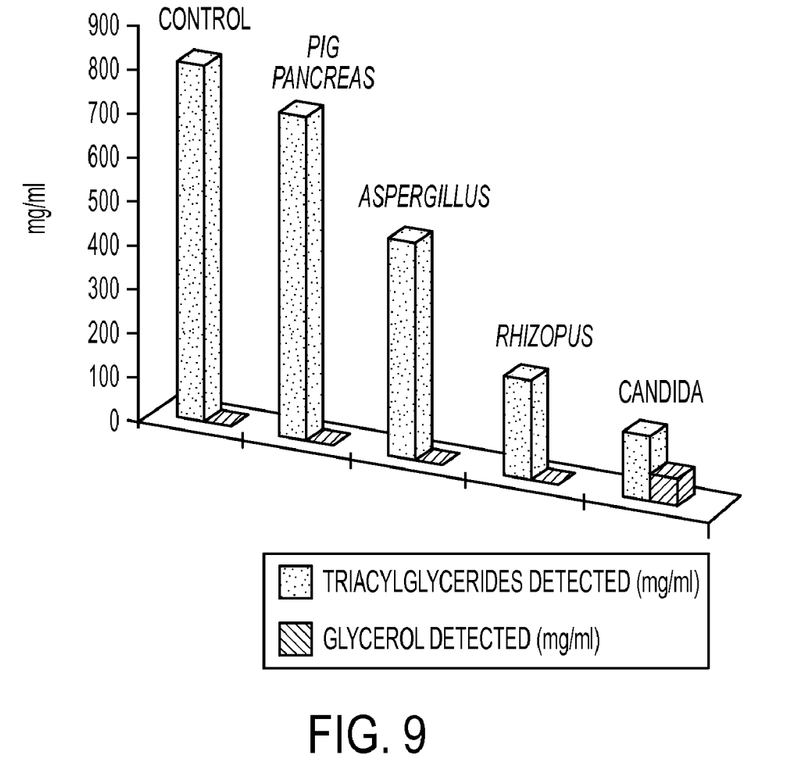
FIG. 9 is a graph comparing the action of 4 sources of lipases on the breakdown of triacylglycerides and the subsequent production of glycerol from olive oil at pH 4 demonstrating the generality of the observed actions of Candida lipase on other triacylglyceride sources.

FIG. 9 shows the comparative actions of four lipases on triacylglyceride digestion and glycerol production using olive oil. A 30 minute digestion of olive oil triglycerides was made using each of the four lipases (each lipase reaction containing 12,900 FIP Units) using the standard reaction protocol (pH 4). The amount of triacylglycerides and glycerol produced by the lipase reactions were quantitated by HPLC using the methodologies described above.

Control reactions (without lipase) contained 822±2 mg/ml olive oil triacylglycerides and no free glycerol was detected.

Similar results were found using olive oil as a source of triacylglycerides as when using soybean oil. Like with soybean oil, *Candida* lipase was the most effective lipase tested at digesting olive oil triacylglycerides and similarly produced the largest amount of glycerol during the digestive reaction. Similar results were found when using melted shortening (Crisco; Food Lion) dissolved in chloroform as a source of triacylglycerides (data not shown). *Candida* lipase effectively digested shortening triacylglycerides to the similar low levels seen with soybean and olive triacylglycerides at both pH 4 and pH 7 (109 mg/ml and 164 mg/ml remaining triacylglycerides detected, respectively, compared to control 856 mg/ml triacylglycerides). Thus, *Candida* lipase appeared to generally be the most effective enzyme tested to digest lipids.

Example 6

Human Study Using Lipase Formulations

A 1-month study was undertaken to determine the effects of a *Candida* lipase composition on serum triacylglyceride levels in vivo.

Capsules containing 355 mg of the improved lipase composition were administered to three healthy human subjects. All of the components contained in the invention are GRAS (generally regarded as safe). The 355 mg capsules contained the following ingredients:

| Capsule Component | Capsule Amount | Component Role |
| --- | --- | --- |
| *Candida rugosa* lipase | 238 mg (100,000 FIP Units) | Active Ingredient |
| Magnesium Stearate | 2 mg | Lubricant, Anti-Sticking Agent |
| Microcrystalline Cellulose | 96 mg | Emulsifier, Anti-Caking Agent |
| Calcium Carbonate | 19 mg | Additive, Stabilizer |

The participants orally ingested a 355 mg capsule, during each meal, for a 1-month period.

Serum levels of triacylglycerides were determined for each participant before the study began and after the 1-month treatment. The serum levels of triacylglycerides and various other serum proteins were quantitated using local hospital laboratories certified as skilled in the performance of such tests.

The results are shown in the following table:

| Study Participant | Pre-Study TAG Classification | Pre-Study TAG Level (mg/dL) | Post-Study TAG Level (mg/dL) | Percent Reduction in TAG | Post-Study TAG Classification |
| --- | --- | --- | --- | --- | --- |
| A | High | 428 | 236 | 45% Reduction | High |
| B | Borderline High | 183 | 123 | 33% Reduction | Normal |
| C | Normal | 92 | 91 | 1% Reduction | Normal |

The results indicate that *Candida* lipase was able to reduce serum levels of triacylglycerides in the two study participants who started the study with either borderline high or high levels of triacylglycerides. No consistent changes were noted in related parameters tested such as total cholesterol or its derivative (e.g., HDL) in the three study participants. The effect of *Candida* lipase treatment on the participant that started the study with normal serum levels of triacylglycerides was negligible.

It is well-known that triacylglycerides can be produced and stored by adipose and liver cells. It is conceivable that there is a basal level of triacylglycerides in human beings produced by these alternative TAG synthetic sources that is influenced by genetics and environmental factors. As such, the compositions described herein may be best suited for individuals with borderline or high serum levels of triacylglycerides for whom dietary sources and enterocyte activities may contribute to higher serum levels of triacylglycerides.

High serum levels of triacylglycerides (TAG) have been found in many patients that have type 2 diabetes (Bitzur et al., Diabetes Care 32 (suppl 2): S373-S377, 2009). As such, reduction of high serum levels of triacylglycerides by the compositions described herein may help reduce the risk of coronary disease in patients with type 2 diabetes.

REFERENCES

The following documents are hereby incorporated by reference in their entirety.

Bitzur R, Cohen H, Kamari Y, Shaish A, Harats D. Triglycerides and HDL cholesterol: stars or second leads in diabetes? Diabetes Care 32 (suppl 2): S373-S377, 2009.

H W Breuer Curt. Med. Res. Opin. 17(1):60-73, 2001

Food Chemical Codex, 7th Edition. United States Pharmacopeial Convention. pg. 1201-1202, 2011.

Ford E S, Li C, Zhao G, Pearson W S, Mokdad A H. Hypertriglyceridemia and its pharmacologic treatment among US adults. Arch Intern Med, 169(6):572-578, 2009.

J. Gandhi, A. Wille, A. Steinbach, Ion chromatographic determination of free and total glycerol in biodiesel and biodiesel blends. The Application Notebook, Metrohm e-publication, LC_GC Chromatography online.com Dec. 2, 2009.

Gopinath S. C. B., et al. World J Review of MICB and Biotechnol., 19(7):681-689, 2003.

Graham D Y. Enzyme replacement therapy of exocrine pancreatic insufficiency in man. Relations between in vitro enzyme activities and in vivo potency in commercial pancreatic extracts New England Journal of Medicine 296: 1314-1317, 1977.

Jensen R G, deJong F A, Clark R M. Determination of lipase specificity. Lipids, 18(3):239-252, 1983.

C T Johansen and R A Hegele, Curr. Opin. Lipidol., 22(4): 247-253, 2011.

Y K Keung et. al. South. Med. J. 92(9):912-914, 1999.

Levy, E. Mehran, M. and Seidman, E., Caco-2 cells as a model for intestinal lipoprotein synthesis and secretion. FASEB J, 9:626-635, 1995.

Mansbach II, C. M. and Parthasarathy, S., A re-examination of the fate of glyceride-glycerol in neutral lipid absorption and transport. J. Lipid Research 23:1009-1019, 1982.

Perkins, E. G., American Oil Chem. Soc. Meeting, San Francisco, June 1979.

Podlaha, O. and Töregård, B., A system for identification of triglyglycerides in reverse phase HPLC chromatographs based on equivalent carbon numbers. J. High Resolution Chromatography 5(10)553-558, 1982.

Phan, C. T. and Tso, P., Intestinal lipid absorption and transport. Frontiers in Biosciences 6:d299-319, 2001.

Rhee E P, Cheng S, Larson M G, Walford G A, Lewis G D, McCabe E, Yang E, Farrell L, Fox C S, O'Donnell C J, Carr S A, Vasan R S, Florez J C, Clish C B, Wang T J, Gerszten R E, Lipid profiling identifies a triacylglycerol signature of insulin resistance and improves diabetes prediction in humans. J. Clin. Invest. 121(4):1402-1411, 2011.

Rogalska E, Cudrey C, Ferrato F, Verger R. Stereoselective hydrolysis of triglycerides by animal and microbial lipases. Chirality, 5:24-30, 1993.

Supelco Bulletin 787D, One-step triglyceride separation by reversed phase HPLC without argentation. pg 1-2, Sigma-Aldrich, 1997.

Yang, L-Y. and Kuksis A., Apparent convergence (at 2-monoacylglycerol level) of phosphatidic acid and 2-monoacylglycerol pathways of synthesis of chylomicron triacylglycerols. J. Lipid Research 32:1173-1186, 1991.

U.S. Pat. Nos. 5,260,074; 5,324,514; 5,352,460; and 5,405,621.

U.S. Publication Nos. 2001/0046493; 2003/0017144; and 2008/0279839.

A P van de Woestijne et. al. Obes. Rev. 10.1111 (epub ahead of print) Jul. 12, 2011.

The invention claimed is:

1. A method of reducing serum triacylglyceride levels in a human subject comprising, administering a composition comprising an effective amount of a fungal lipase that (i) exhibits at least 50% of its maximum activity over the pH range of 2.0 to 8.0; and (ii) cleaves all three ester sites of a triglyceride, to a human subject having at least 150 mg/dL of serum triacylglycerides, wherein the effective amount of said fungal lipase comprises at least 25,000 FIP units/meal.

2. The method of claim 1, wherein the fungal lipase comprises at least 180,000 FIP units per gram of the lipase.

3. The method of claim 1, wherein the effective amount of fungal lipase comprises at least 2000 FIP units per gram of fat consumed by said human subject.

4. The method of claim 1, wherein the fungal lipase is a lipase derived from the *Candida* family.

5. The method of claim 1, wherein the composition is administered periodically and over a time period sufficient to reduce serum triacylglycerides by at least 20% compared to the serum triacylglycerides of the human subject before administering the composition to said human.

6. The method of claim 5, wherein the composition is administered for at least one week.

7. The method of claim 4, wherein the fungal lipase is a lipase derived from *Candida rugosa*.

8. The method of claim 1, wherein the effective amount of said fungal lipase comprises at least 50,000 FIP units/meal.

9. The method of claim 8, wherein the effective amount of said fungal lipase comprises at least 100,000 HP units/meal.

10. The method of claim 5, wherein the composition is administered periodically and over a time period sufficient to reduce serum triacylglycerides by at least 30% compared to the serum triacylglycerides of the human subject before administering the composition to said human.

11. The method of claim 1, wherein the composition is administered for at least four weeks.

12. The method of claim 2, wherein the fungal lipase is a lipase derived from *Candida rugosa*.

13. the method of claim 3, wherein the fungal lipase is a lipase derived from *Candida rugosa*.

14. The method of claim 5, wherein the fungal lipase is a lipase derived from *Candida rugosa*.

15. The method of claim 6, wherein the fungal lipase is a lipase derived from *Candida rugosa*.

16. The method of claim 8, wherein the fungal lipase is a lipase derived from *Candida rugosa*.

17. The method of claim 9, wherein the fungal lipase is a lipase derived from *Candida rugosa*.

18. The method of claim 10, wherein the fungal lipase is a lipase derived from *Candida rugosa*.

19. The method of claim 11, wherein the fungal lipase is a lipase derived from *Candida rugosa*.

20. A method of reducing serum triacylglycerides levels in a human subject comprising, administering a composition comprising an effective amount of a fungal lipase derived from *Candida rugosa*, to a human subject having at least 150 mg/dL of serum triacylglycerides, wherein the effective amount of said fungal lipase comprises at least 100,000 FIP units/meal, and further wherein the composition is administered for at least four weeks.

* * * * *

UNITED STATES PATENT AND TRADEMARK OFFICE
CERTIFICATE OF CORRECTION

| | | |
|---|---|---|
| PATENT NO. | : 8,268,305 B1 | Page 1 of 1 |
| APPLICATION NO. | : 13/244131 | |
| DATED | : September 18, 2012 | |
| INVENTOR(S) | : Schuler et al. | |

It is certified that error appears in the above-identified patent and that said Letters Patent is hereby corrected as shown below:

In the Claims

Col. 14, line 18 Claim 9, change "100,000 HP units/meal" to — 100,000 FIP units/meal —.

Signed and Sealed this
Twenty-second Day of September, 2015

Michelle K. Lee
*Director of the United States Patent and Trademark Office*